US009827032B2

(12) United States Patent
Ishikawa et al.

(10) Patent No.: US 9,827,032 B2
(45) Date of Patent: Nov. 28, 2017

(54) PLASMA TREATMENT SYSTEM

(71) Applicant: OLYMPUS CORPORATION, Hachioji-shi, Tokyo (JP)

(72) Inventors: Manabu Ishikawa, Hachioji (JP); Shuichi Kimura, Hachioji (JP); Koichiro Watanabe, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/187,477

(22) Filed: Jun. 20, 2016

(65) Prior Publication Data

US 2016/0302843 A1  Oct. 20, 2016

Related U.S. Application Data

(63) Continuation of application No. PCT/JP2015/059756, filed on Mar. 27, 2015.

(30) Foreign Application Priority Data

Apr. 11, 2014  (JP) .................................. 2014-082287

(51) Int. Cl.
*A61B 18/18* (2006.01)
*A61B 18/04* (2006.01)
(Continued)

(52) U.S. Cl.
CPC ........ *A61B 18/042* (2013.01); *A61B 18/1206* (2013.01); *A61B 18/14* (2013.01);
(Continued)

(58) Field of Classification Search
CPC .................. A61B 18/14; A61B 18/042; A61B 2018/00767
See application file for complete search history.

(56) References Cited

U.S. PATENT DOCUMENTS 6,582,423 B1 * 6/2003 Thapliyal ........... A61B 18/1206
128/898
6,929,643 B2  8/2005 Ohyama et al.
(Continued)

FOREIGN PATENT DOCUMENTS

| JP | 2003-305054 A | 10/2003 |
| JP | 2011-045756 A | 3/2011 |
| JP | 2013-211153 A | 10/2013 |

OTHER PUBLICATIONS

Oct. 20, 2016 International Preliminary Report on Patentability issued in PCT/JP2015/059756.
(Continued)

*Primary Examiner* — Michael Peffley
*Assistant Examiner* — Amanda Zink
(74) *Attorney, Agent, or Firm* — Oliff PLC

(57) ABSTRACT

A plasma treatment system includes a spout, a suction hole, a first electrode and a second electrode, an impedance acquisition unit, a liquid volume adjustment unit, and a first control unit. The first electrode and a second electrode are configured to generate plasma to treat a living tissue by the application of a voltage. The impedance acquisition unit acquires impedance between the first electrode and the second electrode. The liquid volume adjustment unit adjusts the supply volume or suction volume of the electrically conductive solution. The first control unit controls the liquid volume adjustment unit to increase or decrease the supply volume or suction volume of the electrically conductive solution based on the impedance.

1 Claim, 6 Drawing Sheets

(51) Int. Cl.
*A61B 18/12* (2006.01)
*A61B 18/14* (2006.01)
*A61B 18/00* (2006.01)

(52) U.S. Cl.
CPC .............. *A61B 2018/00577* (2013.01); *A61B 2018/00714* (2013.01); *A61B 2018/00767* (2013.01); *A61B 2018/00791* (2013.01); *A61B 2018/00827* (2013.01); *A61B 2018/00875* (2013.01); *A61B 2018/1472* (2013.01); *A61B 2218/007* (2013.01)

(56) References Cited

U.S. PATENT DOCUMENTS

| | | | |
|---|---|---|---|
| 2004/0019351 A1 | 1/2004 | Ohyama et al. | |
| 2007/0049919 A1* | 3/2007 | Lee, Jr. .............. | A61B 18/1233 606/34 |
| 2008/0167645 A1* | 7/2008 | Woloszko .......... | A61B 18/1206 606/40 |

OTHER PUBLICATIONS

Jun. 23, 2015 Search Report issued in International Patent Application No. PCT/JP2015/059756.

Nov. 17, 2015 Office Action issued in Japanese Patent Application No. 2015-544260.

* cited by examiner

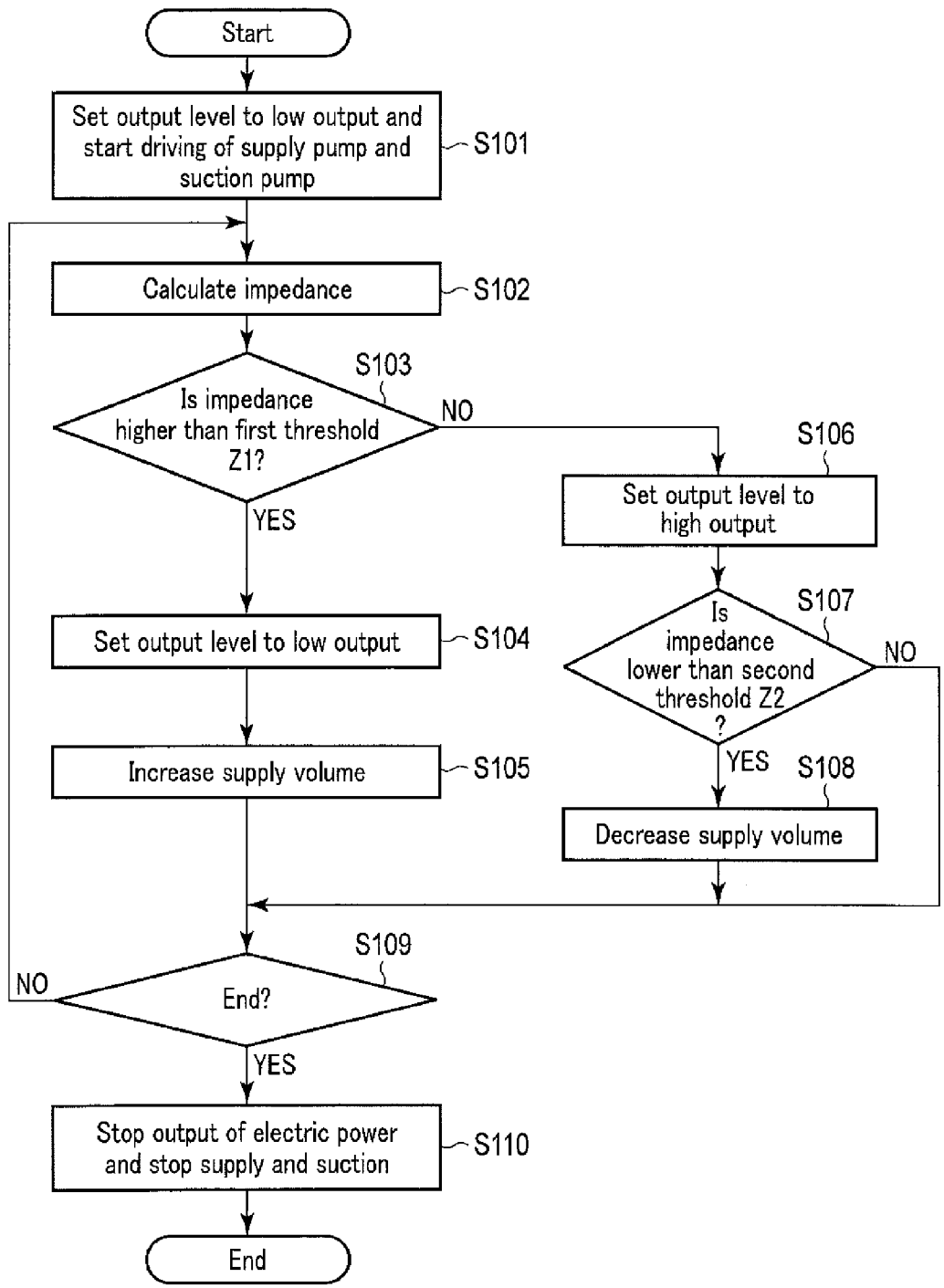
F I G. 4

PLASMA TREATMENT SYSTEM

CROSS-REFERENCE TO RELATED APPLICATIONS

This application is a Continuation Application of PCT Application No. PCT/JP2015/059756, filed Mar. 27, 2015 and based upon and claiming the benefit of priority from prior Japanese Patent Application No. 2014-082287, filed Apr. 11, 2014, the entire contents of all of which are incorporated herein by reference.

BACKGROUND OF THE INVENTION

1. Field of the Invention

The present invention relates to a plasma treatment system.

2. Description of the Related Art

There has been known a treatment method which generates plasma by passing a radio-frequency electric current across two electrodes immersed in a physiological saline, and evaporates and ablates a living tissue by the plasma. For example, Jpn. Pat. Appln. KOKAI Publication No. 2011-045756 has disclosed a system for electrosurgical treatments that is used in the above treatment. The system disclosed in Jpn. Pat. Appln. KOKAI Publication No. 2011-045756 is provided with two electrodes and a fluid supply element which forms a fluid channel to dampen the electrodes. When a radio-frequency voltage is applied across these two electrodes, part of the fluid present in the vicinity of the electrodes vaporizes, and ionized plasma is generated. Jpn. Pat. Appln. KOKAI Publication No. 2011-045756 has disclosed that charged particles of the plasma generated as above collide with a living tissue which is a target, leading to molecular breakdown or molecular collapse in the living tissue. The treatment in which, for example, the living tissue that is a treatment target ablates in this way is called a low-temperature ablation treatment. Jpn. Pat. Appln. KOKAI Publication No. 2011-045756 has disclosed that the above-mentioned system can be used in the field of otorhinolaryngology.

BRIEF SUMMARY OF THE INVENTION

According to an aspect of the invention, a plasma treatment system includes a spout configured to discharge an electrically conductive solution; a suction hole configured to suction the electrically conductive solution; a first electrode and a second electrode provided so that their positional relation is fixed to a position so that the first electrode and the second electrode are immersed in the electrically conductive solution which is discharged from the spout and which is suctioned from the suction hole, the first electrode and the second electrode being configured to generate plasma to treat a living tissue by application of a voltage; an impedance acquisition unit which acquires impedance between the first electrode and the second electrode; a liquid volume adjustment unit which adjusts a supply volume or a suction volume of the electrically conductive solution; and a first control unit which controls the liquid volume adjustment unit to increase or decrease the supply volume or the suction volume of the electrically conductive solution based on the impedance.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a flowchart showing an example of the operation of the plasma treatment system according to a first embodiment;

DETAILED DESCRIPTION OF THE INVENTION

[First Embodiment]

Figure 1:
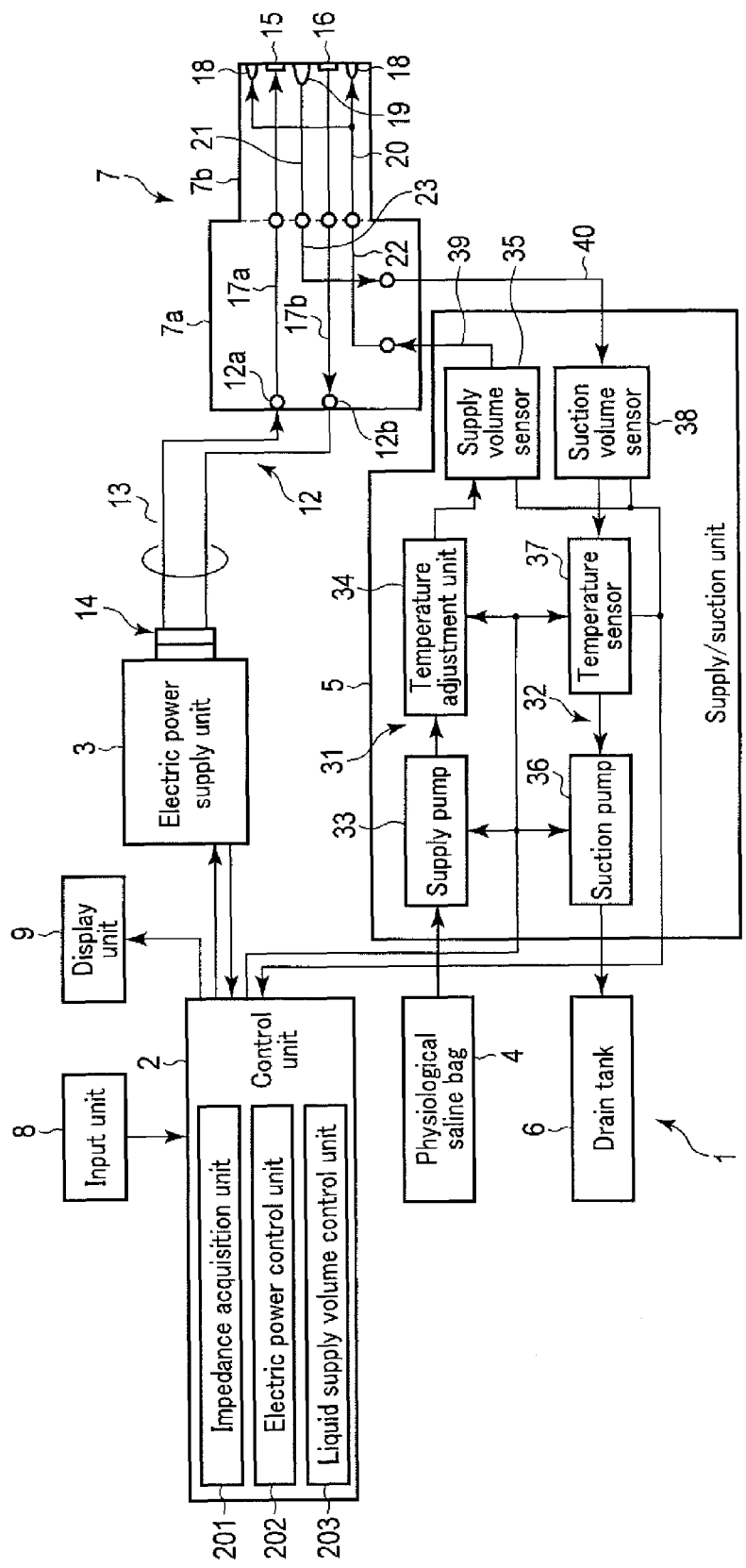
FIG. 1 is a block diagram showing an overview of a configuration example of a plasma treatment system according to one embodiment of the present invention.

A first embodiment of the present invention is described with reference to the drawings. FIG. 1 is a block diagram showing an overview of the overall configuration of a plasma treatment system 1 according to the present embodiment. This plasma treatment system 1 is used in a treatment to generate plasma, and to evaporate by the plasma a living tissue which is a treatment target. As a result of the ablation of the living tissue using the plasma, heat damage to the periphery of the ablated tissue is relatively reduced, and a minimally invasive treatment is achieved. The plasma treatment system 1 is used, for example, in the field of otorhinolaryngology for the ablation of tonsillar tissue. The plasma treatment system 1 may also be used, for example, in the field of orthopedics for synovectomy or chondrectomy, or may also be used in abdominal surgery in general for the resection of organs (a liver in particular).

The plasma treatment system 1 comprises a control unit 2 which controls each part of the system, a plasma treatment instrument 7 which subjects a living tissue to a treatment by plasma, and an electric power supply unit 3 which supplies radio-frequency (RF) electric power to the plasma treatment instrument 7. The plasma treatment instrument 7 has a holding portion 7a for a user to grasp the plasma treatment instrument 7, and a probe 7b provided on the distal side of the holding portion 7a. Active electrodes 15 and return electrodes 16 are provided at the distal end of the probe 7b. The plasma treatment instrument 7 generates plasma at the distal end of the probe 7b by the passage of an electric current across the active electrodes 15 and the return electrodes 16.

The plasma treatment system 1 comprises a physiological saline bag 4 which is filled with a physiological saline to supply, to the distal end of the probe 7b, the physiological saline that is an electrically conductive solution necessary to generate plasma at the distal end of the probe 7b, a supply/suction unit 5 which supplies and suctions the physiological saline, and a drain tank 6 which receives the suctioned physiological saline. A commercially available material can be used as the physiological saline bag 4. The supply of the physiological saline to the probe 7b and the suction of the physiological saline from the probe 7b are adjusted by the supply/suction unit 5. Thus, the supply/suction unit 5 functions as a flow volume adjusting unit which adjusts the supply volume or suction volume of the electrically conductive solution. The electrically conductive solution is preferably, but not limited to, the physiological saline which is electrically conductive and which is harmless to humans. Any other solution which is an electrically conductive liquid and is harmless to humans may be used.

Although not shown, the control unit 2 has a processing unit which has an operational processing function such as a CPU or an ASIC, and a memory to store processing programs, preset or suitably set numerical information, a control table, and others. The control unit 2 has components that are included in a general electronic computer.

A display unit 9 which displays, for example, information regarding treatments, set information, and detected information, is connected to the control unit 2. Various display devices that are generally used, such as a liquid crystal display, and a pilot lamp including an LED lamp, can be used in the display unit 9.

An input unit 8 including an input panel or a keyboard to input and set information is connected to the control unit 2 in a wired or wireless manner. The input unit 8 includes switches to conduct a plasma treatment that will be described later. These switches include, for example, a switch to set the supply and suction of the physiological saline, and a foot switch to generate plasma at the distal end of the probe 7b to conduct the treatment. These switches may be independently provided, may be provided in the electric power supply unit 3, in the supply/suction unit 5, in the control unit 2, or may be provided in the holding portion 7a of the plasma treatment instrument 7. For example, the switches provided in the holding portion 7a may take charge of the function of the above-mentioned foot switch.

The electric power supply unit 3 is a radio-frequency electric power supply to output a radio-frequency electric current (voltage) which is, for example, a sinusoidal wave, a triangular wave, or a pulse wave. The electric power supply unit 3 can change the output level. The output level is roughly classified into two levels. That is, the output level includes a high-output level to output high electric power that generates plasma at the distal end of the probe 7b to conduct the treatment, and a low-output level to measure impedance between the active electrodes 15 and the return electrodes 16 as will be described later.

Furthermore, more than one output level is prepared for the high-output level. For example, these output levels are preset, and switched by the control of the control unit 2. For example, an output level suited to each treatment target or each treatment type is prepared, and an output level is selected suitably to the treatment to be conducted. The output level is adjusted in accordance with various conditions during a treatment; for example, the size of a treatment target part or the state of a tissue, the state of a tissue around the treatment target part, or the progress of the treatment. The condition during the treatment may be input by the user, may be determined by the control unit 2 in accordance with the later-described impedance between the active electrodes 15 and the return electrodes 16, for example, or may be determined by the control unit 2 in accordance with the output of some other sensor. Moreover, an output level suited to each of the types of, for example, plasma treatment instruments having different shapes of the active electrodes is prepared, and an output level is selected suitable to the type of plasma treatment instrument. The user may select a plasma treatment instrument and thereby select an output level suited to the type of plasma treatment instrument. For example, the plasma treatment instrument may be equipped with a memory to store ID information, and when the plasma. treatment instrument is coupled to the electric power supply unit 3, the ID information may be read from the treatment instrument by the control unit 2, and a suitable level may be set. Thus, the high-output level, for example, corresponds to a first electric power which generates plasma, and for example, the low-output level corresponds to a second electric power, which is lower than the first electric power and which does not generate plasma.

The electric power supply unit 3 can acquire a voltage value applied across the active electrodes 15 and the return electrodes 16, and an electric current value running therethrough. The electric power supply unit 3 outputs the acquired voltage value and electric current value to the control unit 2. The control unit 2 calculates impedance between the active electrodes 15 and the return electrodes 16, as will be described later, on the basis of the voltage value and the electric current value.

The plasma treatment instrument 7 is described in detail here. The plasma treatment instrument 7 is a disposable type treatment instrument. As described above, the plasma treatment instrument 7 includes the holding portion 7a and the probe 7b. Terminals 12a and 12b, to which the radio-frequency electric power that is output from the electric power supply unit 3 is supplied, are provided on the proximal side of the holding portion 7a. Electric power supply cables 13 are removably connected at one end to these terminals 12a and 12b. The electric power supply cables 13 are removably connected at the other end to the electric power supply unit 3 via a connector 14. These electric power supply cables 13 are preferably electromagnetically shielded cables or the like so that radio-frequency electromagnetic waves do not leak out and external noise is not superimposed on a signal running through the electric power supply cables 13. For example, a unit in which the connector 14 and the electric power supply cables 13 are integrated can be used for each treatment, and each unit can be disposed of after use. The plasma treatment instrument 7 and the electric power supply cables 13 can be attached to and detached from each other at the terminals 12a and 12b, and the plasma treatment instrument 7 may be replaced in each treatment. If the holding portion 7a and the probe 7b are detachable from each other, the probe 7b alone may be replaced in each treatment.

The plasma treatment instrument 7 is provided with a memory to store identification numbers and characteristics of the treatment instrument. When the plasma treatment instrument 7 is connected to the control unit 2, the information in this memory may be read by the control unit 2. Various setting conditions of the plasma treatment instrument such as proper output levels and the supply volume and suction volume of the physiological saline are recorded in the memory in the plasma treatment instrument 7, and the control unit 2 can read this information. Model information alone may be recorded in the memory in the plasma treatment instrument 7, output levels suited to multiple models, and the supply volume and suction volume of the physiological saline may be recorded in the memory in the control unit 2. In this case, the control unit 2 can read the model information from the memory in the plasma treatment instrument 7, and read information such as a corresponding output level and the supply volume and suction volume of the physiological saline that are recorded in the control unit 2. Information is thus recorded in the plasma treatment instrument 7, so that the user does not need to set various conditions.

Figure 2:
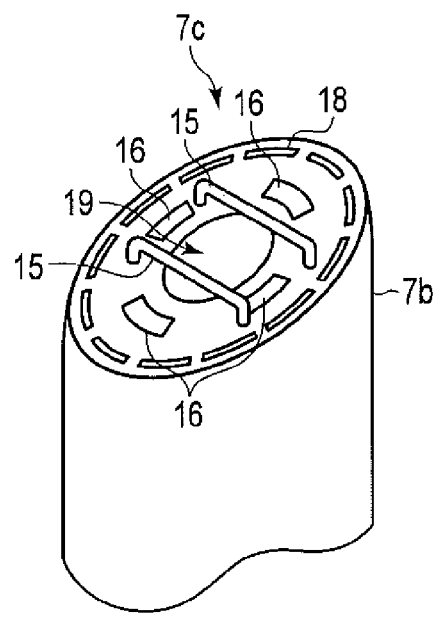
FIG. 2 is a perspective view showing a configuration example of the distal end of a probe of a plasma treatment instrument.
Figure 3:
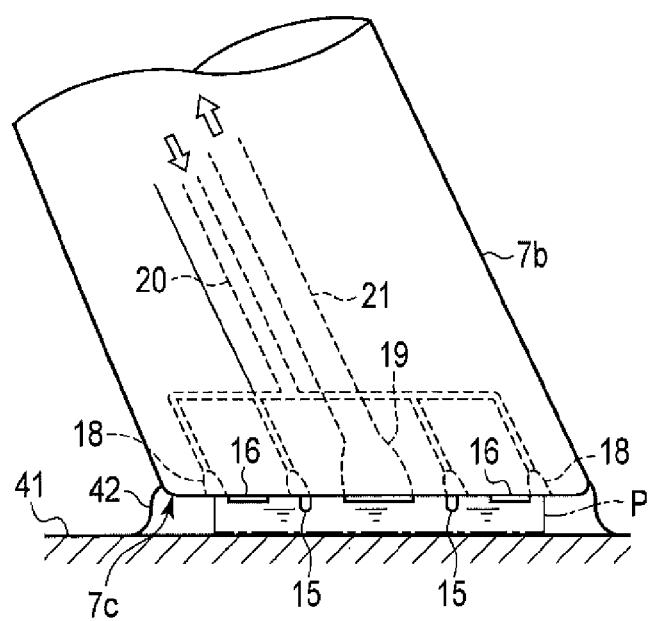
FIG. 3 is a side view showing a configuration example of the distal end of the probe of the plasma treatment instrument.

As shown in FIG. 2 and FIG. 3, the probe 7b according to the present embodiment is provided in its distal face 7c with the active electrodes 15 and the return electrodes 16. Although the multiple active electrodes 15 and the multiple return electrodes 16 are provided in the example shown in FIG. 2, only at least one active electrode 15 and at least one return electrode 16 must be provided. The active electrodes 15 are connected to the terminal 12a by an internal wiring line 17a. The return electrodes 16 are connected to the terminal 12b by an internal wiring line 17b. The internal wiring line 17a and the internal wiring line 17b are inserted through the holding portion 7a and the probe 7b. The active electrodes 15 and the return electrodes 16 are connected to the electric power supply unit 3 via the internal wiring line 17a and the internal wiring line 17b, and via the electric power supply cables 13.

In the vicinity of the outer circumference of a distal face 7c of the probe 7b, spouts 18 having arc-shaped openings are provided along the outer circumference. A circular suction hole 19 is provided in the central part of the distal face 7c. The active electrodes 15 are provided across the suction hole 19. Thus, the spouts 18 and the suction hole 19 are disposed so that the active electrodes 15 and the return electrodes 16 are put between the spouts 18 and the suction hole 19. One end of a first internal tube 20 is connected to the spouts 18, and the first internal tube 20 passes through the probe 7b. One end of a second internal tube 21 is connected to the suction hole 19, and the second internal tube 21 passes through the probe 7b. The first internal tube 20 is connected to a first connection tube 22. The second internal tube 21 is connected to a second connection tube 23. Although the internal tube is coupled to the connection tube in the example shown in the present embodiment, the internal tube and the connection tube may be one tube.

The return electrodes 16 and the spouts 18 do not always need to be disposed on the distal face 7c, and may be disposed on the cylindrical side surface of the probe 7b. A sheath through which the probe 7b is inserted may be provided, and spouts may be formed in the distal end in a space between this sheath and the probe 7b. The spouts 18 must be disposed closer to the outer circumferential side or the side of the holding portion 7a than the return electrodes 16 so that the active electrodes 15 and the return electrodes 16 are immersed in the physiological saline. The active electrodes 15 and the suction hole 19 are preferably, but not exclusively, provided in the distal face 7c of the probe 7b for ease of the treatment. The spouts and the suction hole may be disposed in reverse. That is, the spout may be provided in the center of the distal face 7c of the probe 7b, and the suction holes may be disposed along the outer circumference of the distal face 7c.

The distal face 7c of the probe 7b is inclined instead of being perpendicular to the central axis of the circular cylindrical probe 7b so that the distal face 7c faces the surface of a living tissue treatment target when the user grasps and uses the plasma treatment instrument 7. This improves operability.

When the treatment with the plasma treatment instrument 7 is conducted, the distal end of the probe 7b is perfused with the physiological saline which is supplied from the spouts 18 and which is suctioned from the suction hole 19. As shown in FIG. 3, when the distal face of the probe 7b is located in the vicinity of a living tissue 41 which is a treatment target, a physiological saline 42 is present within a given range. That is, a perfusion layer of the physiological saline is formed in the distal face of the probe 7b and in its outer circumferential surface located in the vicinity of the distal end. As a result, the active electrodes 15 and the return electrodes 16 are immersed in the physiological saline.

While the active electrodes 15 and the return electrodes 16 are immersed in the physiological saline 42, a radio-frequency voltage is applied across the active electrodes 15 and the return electrodes 16. In this instance, the physiological saline 42 vaporizes in the vicinity of the active electrodes 15 and the return electrodes 16, and a vapor layer is formed. If a voltage is further applied across the active electrodes 15 and the return electrodes 16, a breakdown takes place in the vapor layer, and plasma is generated. A region in which this plasma is generated is referred to as a plasma generation region P. The living tissue 41 located in the vicinity of the plasma generation region P evaporates due to the generated plasma. The evaporated living tissue and fragments of the broken living tissue are suctioned into the suction hole 19 together with the physiological saline.

While there are a number of unclear points in the principle of the evaporation of the living tissue in the vicinity of the plasma generation region P, the action of, for example, an OH radical is considered to be the cause. It is also considered that molecules of the physiological saline 42 dissociate in the plasma generation region P, and positive ions having high energy are generated accordingly, so that the molecules in the surface of the tissue are pared off by the collision of the positive ions with the living tissue.

Here, the condition for the generation of plasma depends on, for example, structures such as the shapes and inter-electrode distance of the active electrodes 15 and the return electrodes 16, characteristics of an electrically conductive solution used such as the physiological saline, and the volume and temperature of the electrically conductive solution. Thus, the positional relation between the active electrodes 15 and the return electrodes 16 is preferably fixed. Moreover, the volume of the physiological saline is an important factor for proper generation of plasma.

It is important that the surface area of the return electrodes 16 to contact the physiological saline be larger than that of the active electrodes 15. The surface area of the active electrodes 15 is smaller so that the electric current density is higher in the vicinity of the active electrode 15, and desired plasma is generated in the vicinity of the active electrode 15. If the surface area of the active electrodes 15 is larger than the surface area of the return electrodes 16, the return electrodes 16 serve as the active electrodes 15, and desired satisfactory plasma may not be generated.

As described above, for example, the active electrodes 15 and the return electrodes 16 function as a first electrode and a second electrode, and the active electrodes 15 and the return electrodes 16 are provided so that their positional relation is fixed to a position so that the active electrodes 15 and the return electrodes 16 are immersed in the physiological saline which is discharged from the spouts 18 and which is suctioned from the suction hole 19.

Next, the supply/suction unit 5 is described in detail. As described above, the supply/suction unit 5 supplies the physiological saline to the plasma treatment instrument 7 and suctions the physiological saline from the plasma treatment instrument 7. As shown in FIG. 1, the supply/suction unit 5 is provided with a supply line 31 to supply the physiological saline to the plasma treatment instrument 7, and a suction line 32 to suction the physiological saline from the plasma treatment instrument 7.

A supply pump 33, a temperature adjustment unit 34, and a supply volume sensor 35 are provided on the supply line 31 from the upstream side, and a supply tube 39 on the downstream side is connected to the first connection tube 22 of the plasma treatment instrument 7. A suction tube 40 connected to the second connection tube 23 of the plasma treatment instrument 7, a suction volume sensor 38, a temperature sensor 37, and a suction pump 36 are provided on the suction line 32 from the upstream side, and the downstream side of the suction pump 36 is connected to the drain tank 6.

The supply pump 33 operates under the control of the control unit 2, and takes a new physiological saline from the physiological saline bag 4 and supplies the physiological saline to the probe 7*b* of the plasma treatment instrument 7. The supply pump 33 can change the volume of the physiological saline to be supplied to the probe 7*b* under the control of the control unit 2. This supply pump 33 is not particularly limited, but preferably has a structure that is easy to maintain from a hygienic point of view, and is preferably what is known as a roller pump which transports an internal liquid while pressing an elastic tube by the rotation of a roller.

The temperature adjustment unit 34 cools or warms the physiological saline fed from the supply pump 33 under the control of the control unit 2 to adjust the physiological saline to a predetermined range of temperature suited to the treatment. The supply volume sensor 35 is a known flow volume sensor, and detects the supply volume of the physiological saline supplied to the probe 7*b*. The supply volume sensor 35 sends a signal indicating the detected supply volume to the control unit 2. The control unit 2 uses the supply volume detected by the supply volume sensor 35 to adjust the supply volume of the supply pump 33. No supply volume sensor 35 may be provided so that the supply volume is adjusted without feedback control. The supply pump 33, the temperature adjustment unit 34, and the supply volume sensor 35 may be arranged in any order. The supply volume sensor 35 may, depending on its size, for example, be provided in the plasma treatment instrument 7.

The suction pump 36 operates under the control of the control unit 2, and sends, to the drain tank 6, the physiological saline suctioned from the probe 7*b*. The suction pump 36 can change the volume of the physiological saline to be suctioned from the probe 7*b* under the control of the control unit 2. The suction volume sensor 38 detects the suction volume of the physiological saline by the suction pump 36. The suction volume sensor 38 may be a known flow volume sensor, or may be a fluid level sensor or a water level sensor provided in the drain tank 6. The suction volume sensor 38 sends a signal indicating the detected suction volume to the control unit 2. The temperature sensor 37 detects the temperature of the suctioned physiological saline, and sends the detection result to the control unit 2. The control unit 2 uses the suction volume detected by the suction volume sensor 38 to adjust the suction volume of the suction pump 36. No suction volume sensor 38 may be provided so that the suction volume is adjusted without feedback control. The suction pump 36, the temperature sensor 37, and the suction volume sensor 38 may be arranged in any order. The temperature sensor 37 and the suction volume sensor 38 may, depending on their sizes, for example, be provided in the plasma treatment instrument 7.

Next, the control unit 2 is described in detail. The control unit 2 includes an impedance acquisition unit 201, an electric power control unit 202, and a liquid supply volume control unit 203. The impedance acquisition unit 201 calculates impedance between the active electrodes 15 and the return electrodes 16 on the basis of the voltage applied across the active electrodes 15 and the return electrodes 16, and the electric current running therethrough that have been acquired from the electric power supply unit 3.

The electric power control unit 202 controls the electric power supply to the plasma treatment instrument 7 by the electric power supply unit 3 on the basis of the impedance calculated by the impedance acquisition unit 201. The liquid supply volume control unit 203 controls the operations of the supply pump 33 and the suction pump 36 on the basis of the impedance calculated by the impedance acquisition unit 201. That is, the liquid supply volume control unit 203 causes the supply pump 33 to change the supply volume, or causes the suction pump 36 to change the suction volume. Thus, for example, the electric power control unit 202 functions as a second control unit to control an electric power supply unit which supplies electric power to the space between the first electrode and the second electrode. For example, the liquid supply volume control unit 203 functions as a first control unit to control a liquid volume adjustment unit to increase or decrease the supply volume or suction volume of the electrically conductive solution on the basis of the impedance. The control unit 2 may be provided integrally with the electric power supply unit 3.

The operation of the plasma treatment system 1 is described with reference to a flowchart shown in FIG. 4. Processing illustrated in the flowchart shown in FIG. 4 is achieved by operational processing performed in the control unit 2 in accordance with, for example, a program stored in a storage unit included in the control unit 2. This program may be previously recorded in the control unit 2, may be recorded in various media and read from the media by the control unit 2, or may be provided online and acquired by the control unit 2 through communication.

When the user inputs an instruction to start a treatment from the input unit 8, the processing shown in FIG. 4 is started. In step S101, the control unit 2 sets the output level of the plasma treatment instrument 7 to a low output. Here, the low output means a low output so that the impedance between the active electrodes 15 and the return electrodes 16 can be measured, rather than a high output that causes plasma by the plasma treatment instrument 7 to conduct the treatment. The control unit 2 controls the electric power supply unit 3 on the basis of a set low-output value, and causes the electric power supply unit 3 to supply electric power to the plasma treatment instrument 7 at the low output. Here, the electric power may be controlled by a voltage value, or may be controlled by an electric current value. The control unit 2 also causes the supply pump 33 and the suction pump 36 to start the driving of these pumps. The supply volume of the supply pump 33 and the suction volume of the suction pump 36 are set, for example, to a predetermined initial value. This initial value may be set by the user, or may be set to a value previously recorded in the control unit 2 or the plasma treatment instrument 7.

In step S102, the control unit 2 acquires the voltage and electric current supplied to the plasma treatment instrument 7 from the electric power supply unit 3, and calculates impedance between the active electrodes 15 and the return electrodes 16. Although the impedance between the active electrodes 15 and the return electrodes 16 is used as impedance in the example shown in the present embodiment, impedance in any part that reflects the impedance between the active electrodes 15 and the return electrodes 16 may be used as the impedance between the active electrodes 15 and the return electrodes 16, such as impedance between the terminal 12a and the terminal 12b, or impedance between two places in the electric power supply unit 3 including the channel between the active electrodes 15 and the return electrodes 16.

In step S103, the control unit 2 determines whether or not the calculated impedance is higher than a predetermined first threshold Z1. When the distal end of the probe 7b of the plasma treatment instrument 7 is not immersed in the physiological saline to a degree necessary to generate plasma, the impedance between the active electrodes 15 and the return electrodes 16 is extremely high. Even when the active electrodes 15 and the return electrodes 16 are immersed in the physiological saline, the impedance is extremely high if there is a part between the active electrodes 15 and the return electrodes 16 where the physiological saline is discontinuous. The first threshold Z1 is set at an impedance measured, for example, when the distal end of the probe 7b is not immersed in the physiological saline.

When it is determined in step S103 that the impedance is higher than the first threshold Z1, the processing proceeds to step S104. In step S104, the control unit 2 sets the output of the plasma treatment instrument 7 to the low output, and causes the electric power supply unit 3 to supply electric power to the probe 7b at the low output. In step S105, the control unit 2 controls the supply pump 33 to increase the supply volume of the physiological saline. As a result, the volume of the physiological saline present at the distal end of the probe 7b gradually increases. After step S105, the processing proceeds to step S109.

When it is determined in step S103 that the impedance is not higher than the first threshold Z1, the processing proceeds to step S106. The impedance that is not higher than the first threshold Z1 means that the distal end of the probe 7b is immersed in the physiological saline to a degree necessary to generate plasma.

In step S106, the control unit 2 sets the output level of the plasma treatment instrument 7 to a high output. Here, the high output is an output that generates plasma at the distal end of the probe 7b. As described above, the high-output level includes multiple stages of output levels depending on the kind of plasma treatment instrument 7 and methods of treatment. However, these output levels are not distinguished and are referred to as the high output. The control unit 2 controls the electric power supply unit 3 on the basis of the set high-output value, and causes the electric power supply unit 3 to supply electric power to the plasma treatment instrument 7 at the high output. As a result, plasma is generated in the region of the physiological saline where the distal end of the probe 7b is immersed.

The treatment is conducted by this plasma. The output of the electric power supply unit 3 at the high-output level may ordinarily be performed when the control unit 2 sets the high output, or may be performed when the control unit 2 sets the high output and when the foot switch of the input unit 8 is pushed down. Impedance can be calculated on the basis of the voltage value and the electric current value acquired by the electric power supply unit 3 even in a situation in which high electric power that generates plasma is supplied.

In step S107, the control unit 2 determines whether or not the impedance calculated in step S106 is lower than a predetermined second threshold Z2. For example, if more than a proper volume of physiological saline is present at the distal end of the probe 7b, plasma is not efficiently generated at the distal end. In this instance, a lower impedance is measured than when plasma is generated. The impedance measured when the active electrodes 15 and the return electrodes 16 are immersed in a pure physiological saline in which no impurities are mixed is referred to as a first impedance. Impedance measured when plasma is generated is referred to as a second impedance. The second impedance is higher than the first impedance. When the generation of plasma is interrupted because of, for example, the presence of an excessive physiological saline at the distal end of the probe 7b, impurities derived from the tissue are mixed in the physiological saline in which the active electrodes 15 and the return electrodes 16 are immersed. Impedance measured in this instance is referred to as a third impedance. The third impedance is higher than the first impedance, and is lower than the second impedance. As a result, the second threshold Z2 can be set to a value higher than the third impedance and lower than the second impedance.

When it is determined in step S107 that the impedance is not lower than the second threshold Z2, the processing proceeds to step S109. In contrast, when it is determined that the impedance is lower than the second threshold Z2, the processing proceeds to step S108. In step S108, the control unit 2 controls the supply pump 33 to decrease the supply volume of the physiological saline. As a result, the volume of the physiological saline present at the distal end of the probe 7b gradually decreases. After step S108, the processing proceeds to step S109.

In step S109, the control unit 2 determines whether or not the user has input an instruction to end the treatment. When no end instruction is input, the processing returns to step S102, and the processing described above is repeated. In contrast, when an instruction to end is input, the processing proceeds to step S110. In step S110, the control unit 2 causes the electric power supply unit 3 to stop the supply of electric power to the probe 7b. The control unit 2 also causes the supply pump 33 to stop the supply of the physiological saline, and then causes the suction pump 36 to stop the suction. The processing then ends.

According to the plasma treatment system 1 in the present embodiment which performs the processing described above, the supply volume of the physiological saline by the supply pump 33 is increased when there is only a small amount of physiological saline present at the distal end of the probe 7b to generate plasma; or the supply volume of the physiological saline by the supply pump 33 is decreased when too much physiological saline is present at the distal end of the probe 7b to generate plasma. As a result, a volume of the physiological saline suited to the generation of plasma is always maintained at the distal end of the probe 7b.

For example, in a tonsil treatment, there is concern that if a large volume of physiological saline is present, this physiological saline might flow into, for example, the bronchi and complications might occur. The plasma treatment system 1 according to the present embodiment can reduce the risk of such complications. Thus, the plasma treatment system 1 according to the present embodiment is advantageous to the field in which the physiological saline is only perfused at the distal end of the probe 7b to conduct a plasma treatment, particularly as in a treatment in the field of otorhinolaryngology.

High electric power is supplied to the active electrodes 15 and the return electrodes 16 only when the physiological saline is present at the distal end of the probe 7b to a degree than can generate plasma at the distal end of the probe 7b. As a result, safety is further improved because no high voltage is applied across the active electrodes 15 and the return electrodes 16 when the volume of physiological saline is at a low level that generates no plasma.

In the case shown in the example described above, when the output level is the high output and high electric power is supplied to the probe 7b, impedance is calculated on the basis of the voltage value and the electric current value at this moment. However, the present invention is not limited to this. For example, when the electric power supply unit 3 outputs high electric power to generate plasma, the output level may be set to the low output for a short time of, for example, several milliseconds to acquire impedance, and impedance may be calculated on the basis of a voltage value and an electric current value that are acquired at this moment. Impedance is thus always calculated in the low-output state, so that the calculation accuracy of impedance improves.

Although the volume of the physiological saline at the distal end of the probe 7b is controlled by the supply volume of the physiological saline by the supply pump 33 in the case shown in the example described above, the present invention is not limited to this. For example, the suction volume of the physiological saline by the suction pump 36 may be controlled to adjust the volume of the physiological saline at the distal end of the probe 7b. That is, for example, in step S105, the suction volume of the physiological saline may be decreased instead of increasing the supply volume of the physiological saline. Similarly, in step S108, the suction volume of the physiological saline may be increased instead of decreasing the supply volume of the physiological saline. Both the supply volume and suction volume of the physiological saline may be controlled.

When a treatment is conducted with the probe 7b, fragments of the living tissue produced by the treatment are dissolved or dispersed in the physiological saline perfused at the distal end of the probe 7b. As a result, the impedance between the active electrodes 15 and the return electrodes 16 changes depending on the amount of fragments of the living tissue. Thus, according to the measurement of this impedance, it is also possible to monitor the state of the treatment. Accordingly, the plasma treatment system 1 may be configured to adjust the output of the electric power supply unit 3 on the basis of this impedance to conduct a proper treatment. Thus, the electric power control unit 202 may determine the amount of substances derived from the living tissue contained in the physiological saline which is an electrically conductive solution on the basis of the above impedance, and may control the output of the electric power supply unit 3.

Although the user inputs the start and end of a treatment in the present embodiment described, the present invention is not limited to this. For example, a sensor may be provided at the distal end of the probe 7b, and this sensor may be used to start the processing when the distal end of the probe 7b is pressed to a treatment target part, and end the processing when a predetermined time has elapsed.

The plasma treatment instrument 7 according to the present embodiment is provided with the spouts 18 and the suction hole 19, and the probe 7b supplies and suctions the physiological saline, but the present invention is not limited to this. For example, the probe 7b may be provided with the active electrodes 15 and the return electrodes 16, and a supply probe and a suction probe that are separate from the probe 7b may supply and suction the physiological saline. However, when the spouts 18 and the suction hole 19 are provided in the plasma treatment instrument 7 as in the embodiment described above, access to the treatment target is easier, and treatment is more easily conducted. Therefore, the spouts 18 and the suction hole 19 are preferably provided in the plasma treatment instrument 7.

Although the supply pump 33 is used to supply the physiological saline and to adjust the supply volume in the present embodiment, the present invention is not limited to this. For example, the physiological saline bag 4 may be disposed at a high position, and the physiological saline may be supplied to the probe 7b by gravitation. In this instance, a valve may be provided in the supply line so that the supply volume is controlled.

Although the suction pump 36 is used to suction the physiological saline and to adjust the suction volume in the present embodiment, the present invention is not limited to this. For example, the physiological saline may be suctioned from the probe 7b by a wall suction device provided in an operating room. In this instance, a valve may be provided in the supply line so that the suction volume is controlled. Thus, as long as the plasma treatment system 1 comprises the liquid volume adjustment unit to adjust the supply volume or suction volume of, for example, a physiological saline which is an electrically conductive solution, the liquid volume adjustment unit may have any configuration.

The processing shown in FIG. 4 is an example, and the sequence of the processing, for example, can be suitably changed, and some of the processing may be deleted. For example, the liquid supply volume may be adjusted in accordance with impedance, but no change of the output level may be made, or the output level alone may be changed.

Although the plasma treatment system 1 according to the present embodiment can only conduct the treatment to evaporate a living tissue which is a treatment target, the present invention is not limited to this. The plasma treatment system 1 can be configured to be able to coagulate a living tissue which is a treatment target by adjusting the electric power supply to the active electrodes 15 and the return electrodes 16. For example, an output can be set lower when the living tissue is coagulated than when the living tissue is evaporated. The plasma treatment system 1 can be configured so that an evaporation mode and a coagulation mode can be suitably switched. This switching may be performed by the user, or may be set in advance in accordance with, for example, the sequence of the treatment.

[Second Embodiment]

A second embodiment of the present invention is described. Here, the differences between the first embodiment and the second embodiment are described, and the same parts are provided with the same reference marks and are not described. The control unit 2 according to the present embodiment determines various conditions of the distal end of the probe 7b of the plasma treatment instrument 7 on the basis of the impedance between the active electrodes 15 and the return electrodes 16.

Figure 5:
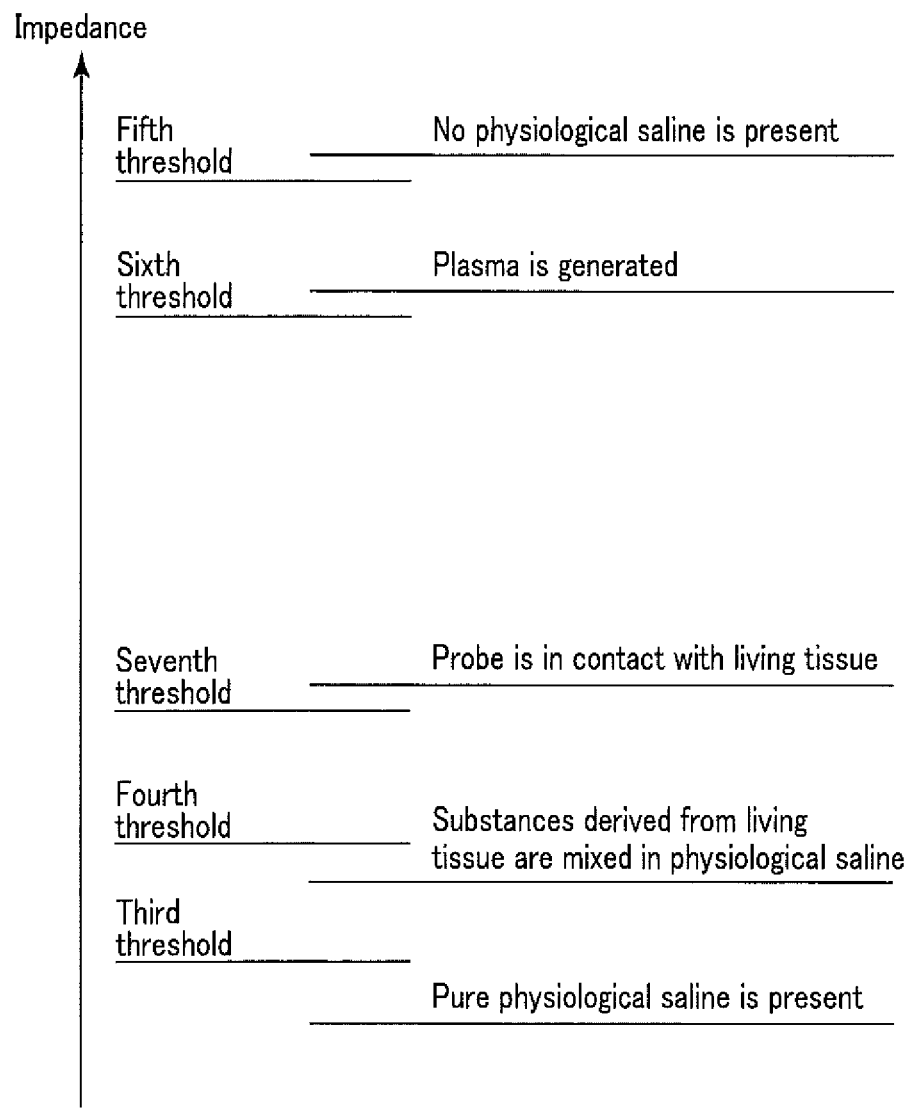
FIG. 5 is a diagram showing an example of the relation between impedance and the state of the probe distal end.

An overview of an example of the relation between the conditions of the distal end of the probe 7b and the impedance between the active electrodes 15 and the return electrodes 16 measured at this moment is shown in FIG. 5. As shown in this drawing, the impedance is lowest when there is a pure physiological saline between the active electrodes 15 and the return electrodes 16. If substances that are produced by the plasma treatment and which are derived from the living tissue are mixed in this physiological saline, the impedance is higher than that in the pure physiological saline. The impedance is higher when the active electrodes 15 and the return electrodes 16 are in contact with the living tissue than when the electrodes are immersed in the physiological saline. The impedance is much higher when plasma is generated between the active electrodes 15 and the return electrodes 16 than when the active electrodes 15 and the return electrodes 16 are in contact with the living tissue. The impedance is further higher when there is no physiological saline between the active electrodes 15 and the return electrodes 16 and no plasma is generated than when plasma is generated. The plasma treatment system 1 according to the present embodiment determines these states on the basis of the impedance, and performs operations suitably to these states.

Figure 6:
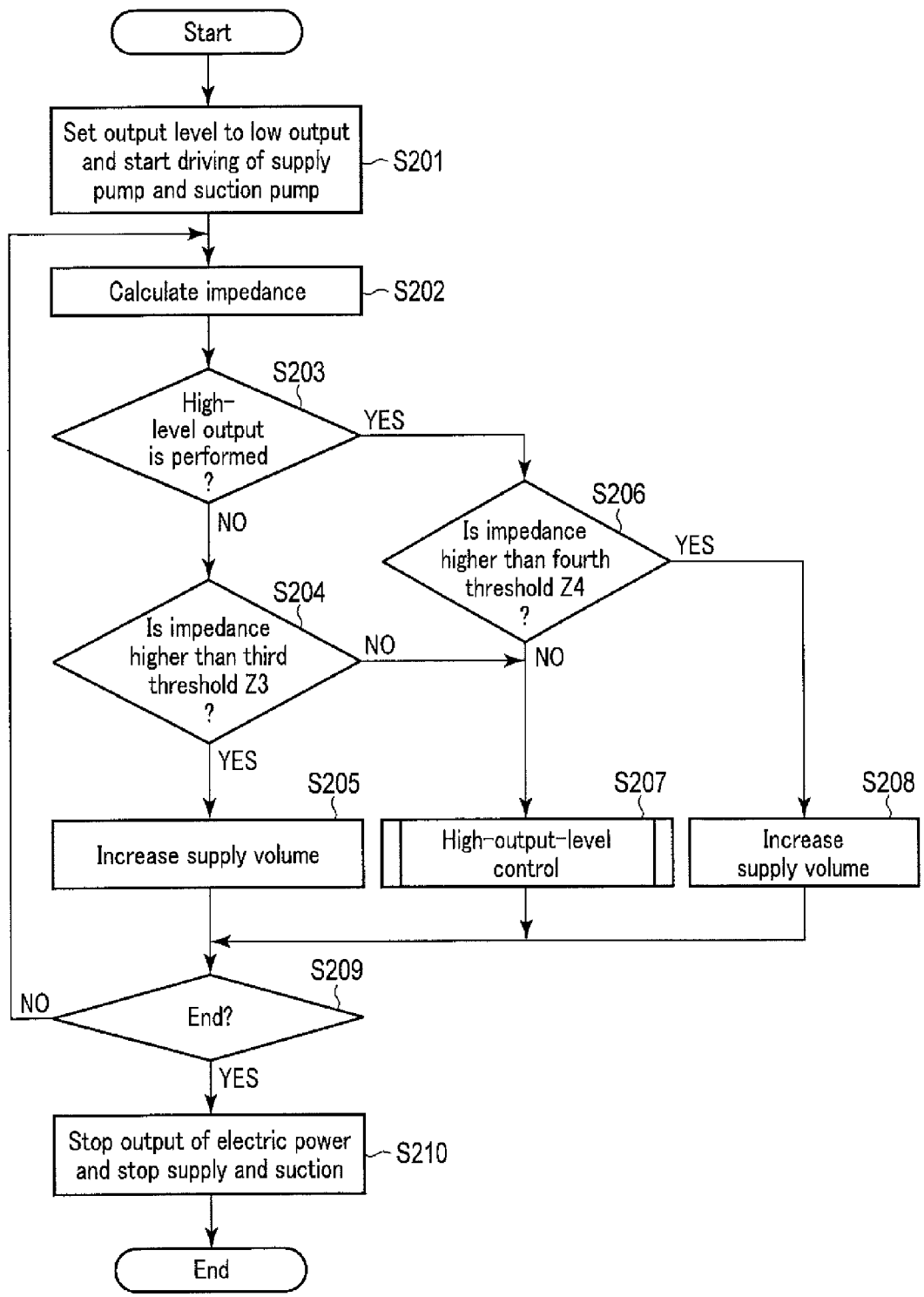
FIG. 6 is a flowchart showing an example of the operation of a plasma treatment system according to a second embodiment.

Processing performed in the control unit 2 in the present embodiment is described with reference to FIG. 5 and a flowchart shown in FIG. 6. In step S201, the control unit 2 sets the output level to the low output, and starts the driving of the supply pump 33 and the suction pump 36. In step S202, the control unit 2 calculates impedance between the active electrodes 15 and the return electrodes 16.

In step S203, the control unit 2 determines whether or not high-level output has been performed in a series of operations. This is because when the high-level output is already performed, there is a possibility that substances derived from the living tissue may be mixed in the physiological saline due to the plasma treatment, so that the threshold used in the subsequent processing is changed depending on if there is or is not such a possibility. When it is determined that the high-level output is performed, the processing proceeds to step S206. In contrast, when it is determined that the high-level output is not performed, the processing proceeds to step S204.

In step S204, the control unit 2 determines whether or not the calculated impedance is higher than a third threshold Z3. Here, as shown in FIG. 5, the third threshold is a value higher than the impedance at which the probe 7b is immersed in the pure physiological saline and lower than the impedance at which the probe 7b is immersed in the physiological saline having substances derived from the living tissue mixed therein. When it is determined that the impedance is higher than the third threshold Z3, the processing proceeds to step S205. In this instance, it is considered that the distal end of the probe 7b is not immersed in the physiological saline. Thus, in step S205, the control unit 2 increases the supply volume of the physiological saline. The processing then proceeds to step S209. In contrast, when it is determined in step S204 that the impedance is not higher than the third threshold Z3, the processing proceeds to step S207.

In step S206, the control unit 2 determines whether or not the calculated impedance is higher than a fourth threshold Z4. Here, as shown in FIG. 5, the fourth threshold is a value higher than the impedance at which the probe 7b is immersed in the physiological saline having substances derived from the living tissue mixed therein and lower than the impedance at which the probe 7b is in contact with the living tissue. When it is determined that the impedance is not higher than the fourth threshold Z4, the processing proceeds to step S207. In this instance, it is considered that the distal end of the probe 7b is immersed in the physiological saline. In step S207, the control unit 2 performs high-output-level control that will be described later. The processing then proceeds to step S209.

When it is determined in step S206 that the impedance is higher than the fourth threshold Z4, the processing proceeds to step S208. In this instance, it is considered that the distal end of the probe 7b is not immersed in the physiological saline. In step S208, the control unit 2 increases the supply volume of the physiological saline. The processing then proceeds to step S209.

In step S209, the control unit 2 determines whether or not the user has input an instruction to end the treatment. When no end instruction is input, the processing returns to step S202, and the processing described above is repeated. In contrast, when an end instruction is input, the processing proceeds to step S210. In step S210, the control unit 2 causes the electric power supply unit 3 to stop the supply of electric power to the probe 7b. The control unit 2 also causes the supply pump 33 to stop the supply of the physiological saline, and then causes the suction pump 36 to stop the suction. The processing then ends.

Figure 7:
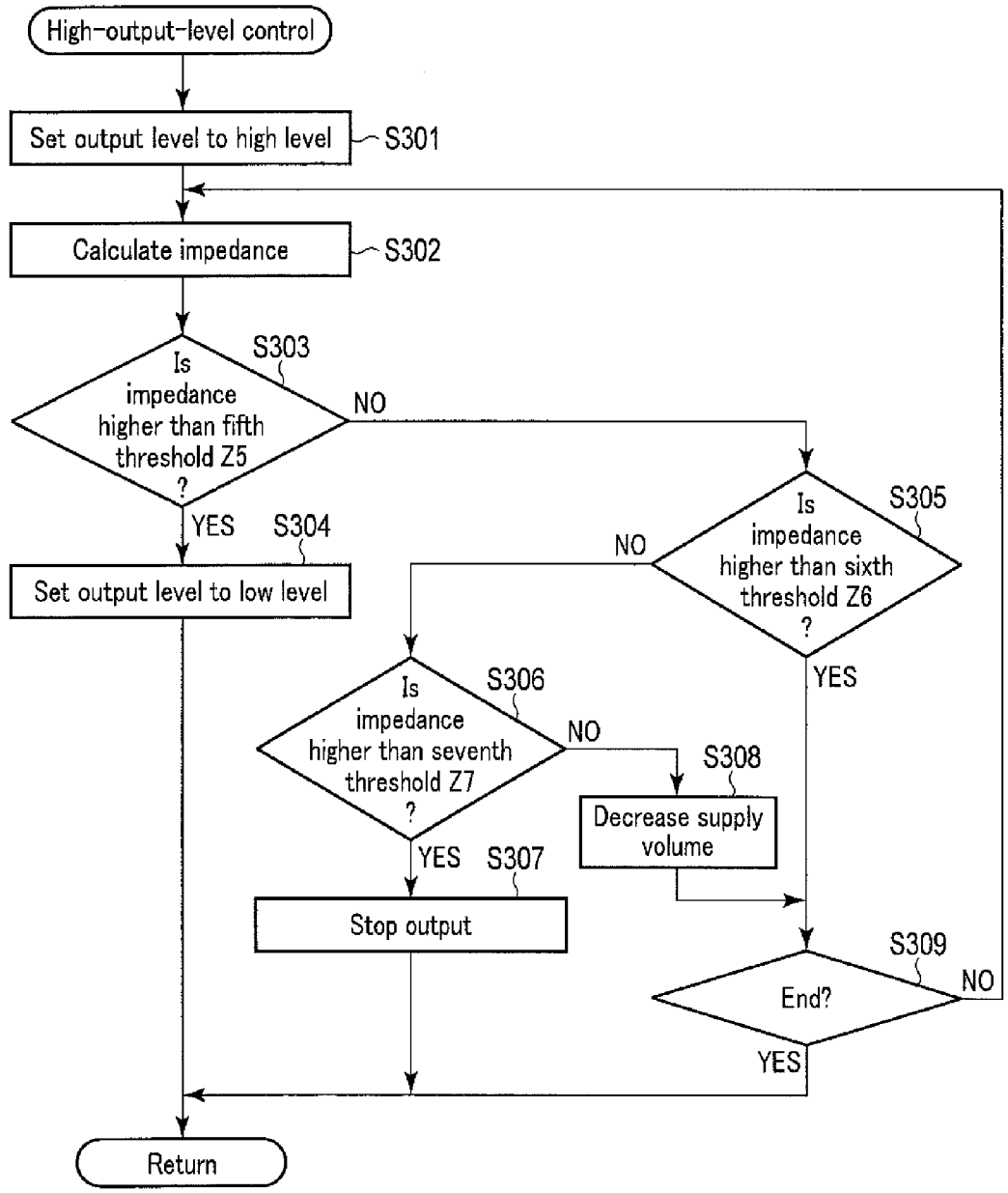
FIG. 7 is a flowchart showing an example of the operation of the plasma treatment system according to the second embodiment.

Next, the high-output-level control performed in step S207 is described with reference to a flowchart shown in FIG. 7. The high-output-level control is control performed when the output level is the high-output level. In step S301, the control unit 2 sets the output level to the high level. The processing then proceeds to step S302. In step S302, the control unit 2 calculates impedance between the active electrodes 15 and the return electrodes 16.

In step S303, the control unit 2 determines whether or not the impedance is higher than a fifth threshold Z5. Here, as shown in FIG. 5, the fifth threshold Z5 is a value slightly lower than the impedance measured when there is no physiological saline at the distal end of the probe 7b. That is, it is considered that there is no physiological saline at the distal end of the probe 7b when the impedance is higher than the fifth threshold Z5. When it is determined that the impedance is higher than the fifth threshold Z5, the processing proceeds to step S304. In step S304, the control unit 2 sets the output level to the low level. The processing then returns to step S207.

When it is determined in step S303 that the impedance is not higher than the fifth threshold Z5, the processing proceeds to step S305. In step S305, the control unit 2 determines whether or not the impedance is higher than a sixth threshold Z6. Here, as shown in FIG. 5, the sixth threshold Z6 is a value slightly lower than the impedance measured when plasma is generated at the distal end of the probe 7b. That is, it is considered that plasma is generated at the distal end of the probe 7b when the impedance is higher than the sixth threshold Z6. When it is determined that the impedance is higher than the sixth threshold Z6, the processing proceeds to step S309.

When it is determined in step S305 that the impedance is not higher than the sixth threshold Z6, the processing proceeds to step S306. In step S306, the control unit 2 determines whether or not the impedance is higher than a seventh threshold 17. Here, as shown in FIG. 5, the seventh threshold Z7 is a value slightly lower than the impedance measured when the distal end of the probe 7b is in contact with the living tissue which is a treatment target. That is, it is considered that the distal end of the probe 7b is in contact with the living tissue when the impedance is higher than the seventh threshold Z7. When it is determined that the impedance is higher than the seventh threshold Z7, the processing proceeds to step S307. If high electric power is supplied between the active electrodes 15 and the return electrodes 16 while the distal end of the probe 7b is in contact with the living tissue, heat damage to the living tissue may be caused. Thus, in step S307, the control unit 2 stops the electric power supply to the active electrodes 15 and the return electrodes 16. The processing then returns to step S207.

When it is determined in step S306 that the impedance is not higher than the seventh threshold Z7, the processing proceeds to step S308. In this instance, it is considered that the physiological saline at the distal end of the probe 7b is excessive, and plasma is not generated efficiently. Thus, in step S308, the control unit 2 decreases the supply volume of the physiological saline. The processing then proceeds to step S309.

In step S309, the control unit 2 determines whether or not the user has input an instruction to end the treatment. When no end instruction is input, the processing returns to step S302, and the processing described above is repeated. In contrast, when an instruction to end is input, the processing proceeds to step S207.

When operating as described above, the plasma treatment system 1 according to the present embodiment determines the state of the distal end of the probe 7b on the basis of the impedance, and can operate suitably to the state. Although the electric power supply to the active electrodes 15 and the return electrodes 16 is stopped when the distal end of the probe 7b is in contact with the living tissue, which is a treatment target in the case shown by way of example in the present embodiment, the present invention is not limited to this. The supplied electric power may be set to the low-output level so that impedance can be measured when the distal end of the probe 7b is in contact with the living tissue which is a treatment target. The supplied electric power may be adjusted suitably to the amount and composition of the living tissues contained in the physiological saline, or the supply volume of the physiological saline may be changed.

According to the present embodiment, it is also possible to obtain advantageous effects similar to those according to the first embodiment. Modifications similar to those in the first embodiment can be made to the plasma treatment system according to the present embodiment.

The embodiments of the present invention described above also include the following invention.

[1] A plasma treatment control unit used together with a plasma treatment instrument and a liquid volume adjustment unit, the plasma treatment instrument comprising a spout configured to discharge an electrically conductive solution, a suction hole configured to suction the electrically conductive solution, a first electrode and a second electrode provided so that their positional relation is fixed to a position so that the first electrode and the second electrode are immersed in the electrically conductive solution which is discharged from the spout and which is suctioned from the suction hole, the plasma treatment instrument treating a living tissue by plasma which is generated by the application of a voltage across the first electrode and the second electrode, the liquid volume adjustment unit adjusting a supply volume or a suction volume of the electrically conductive solution, the plasma treatment control unit comprising:

an impedance acquisition unit which acquires impedance between the first electrode and the second electrode; and a liquid supply volume control unit which causes the liquid volume adjustment unit to increase or decrease the supply volume or the suction volume of the electrically conductive solution on the basis of the impedance.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A plasma treatment system comprising:
a spout configured to discharge an electrically conductive solution;
a suction hole configured to suction the electrically conductive solution;
a first electrode and a second electrode provided so that their positional relation is fixed to a position so that the first electrode and the second electrode are immersed in the electrically conductive solution which is discharged from the spout and which is suctioned from the suction hole;
an electric power supply unit which supplies first electric power to generate plasma to the first electrode and the second electrode;
an impedance acquisition unit which acquires impedance between the first electrode and the second electrode;
a liquid volume adjustment unit which adjusts a supply volume or a suction volume of the electrically conductive solution; and
a control unit which outputs a control signal to the liquid volume adjustment unit when the impedance acquired during a supply of the first electric power becomes lower than a first threshold, the control signal causing the liquid volume adjustment unit to conduct at least one of a decrease of the supply volume of the electrically conductive solution and an increase of the suction volume of the electrically conductive solution,
wherein the electric power supply unit temporarily supplies second electric power which is electric power lower than the first electric power to the first electrode and the second electrode during supply of the first electric power, and
wherein when the impedance acquired during supply of the second electric power becomes lower than the first threshold, the control unit outputs a control signal to the liquid volume adjustment unit to cause the liquid volume adjustment unit to conduct at least one of the decrease of the supply volume of the electrically conductive solution and the increase of the suction volume of the electrically conductive solution.

* * * * *